United States Patent [19]

Duke

[11] 4,261,851
[45] Apr. 14, 1981

[54] LOW-IRRITATING DETERGENT COMPOSITION
[75] Inventor: Roland P. Duke, Fareham, England
[73] Assignee: Johnson & Johnson Products, Inc., New Brunswick, N.J.
[21] Appl. No.: 59,836
[22] Filed: Jul. 23, 1979
[51] Int. Cl.$^3$ .......................... C11D 1/72; C11D 1/83
[52] U.S. Cl. .......................... 252/174.21; 252/174.22; 252/545; 252/546; 252/551; 260/410.6
[58] Field of Search ..................... 252/174.21, 174.22, 252/89, DIG. 1, 13, 545, 546, 551; 260/410.6

[56] References Cited

U.S. PATENT DOCUMENTS

| | | | |
|---|---|---|---|
| 2,329,394 | 9/1943 | DeGroote et al. | 260/404.8 |
| 2,353,701 | 7/1944 | DeGroote et al. | 260/404.8 |
| 2,549,437 | 4/1951 | DeGroote et al. | 260/410.6 |
| 3,067,222 | 12/1962 | Anderson | 260/410.6 |
| 3,141,897 | 7/1964 | Creclius et al. | 260/404.8 |
| 3,957,970 | 5/1976 | Korkis | 424/70 |
| 4,154,706 | 5/1979 | Kenkare et al. | 252/547 |
| 4,177,171 | 12/1979 | Walts | 252/541 |

Primary Examiner—P. E. Willis, Jr.
Attorney, Agent, or Firm—Steven P. Berman

[57] ABSTRACT

A detergent composition for personal use such as skin cleansing or care of the hair, comprising at least two surfactants, one being of a particular nonionic type and another being of a different type such as an amphoteric-/anionic surfactant. The nonionic surfactant has a thickening effect and is typified by diabasic and tribasic acid reaction products of alkoxylated polyol fatty esters.

5 Claims, No Drawings

LOW-IRRITATING DETERGENT COMPOSITION

The present invention relates to liquid detergent compositions for personal use, that is to say capable of use in contact with the skin of the person, usually for cleansing the skin or hair, such as a shampoo formulation or a bath additive. The invention finds application in such compositions generally, but is especially useful in those detergent compositions which have relatively low ocular irritation and yet have large foam volume and improved foam stability.

Detergent compositions, like most types of liquid cleaning agents, generally comprise a mixture of one or more surfactants as the active ingredient, perfumes, colouring agents, thickeners, etc. The surfactants have two portions: (1) hydrophobic hydrocarbon chain miscible with organic materials and (2) a hydrophilic end-group miscible with water. When such a surfactant contacts a particle of soil, the hydrocarbon chains mix therewith and the hydrophilic end-groups are presented to the aqueous solution. This process of emulsification allows the soil, which otherwise would resist removal by the water, to be cleaned from the body thereby. The surfactants may be classified as anionic, cationic, non-ionic, or amphoteric, depending upon the character of the end-groups.

It is desirable that detergent compositions have high foam volume and foam stability, particularly if they are used as shampoos. The amount of foam or lather produced by a shampoo has a direct bearing on the perceived efficiency with which it cleans the hair. The stability of that foam indicates how long it will keep the hair lathered. Generally speaking, the larger the volume of foam produced and the more stable the foam, the more efficient the perceived cleaning action of the shampoo.

A further desirable property for a shampoo, especially one designed for use by children, is that it have low ocular irritation. Because a shampoo may accidentally contact the ocular mucosa during use, especially use by children, one which causes relatively little irritation is both desirable and useful.

Non-irritating detergent compositions have been known and have been in use for some time. U.S. Pat. Nos. 2,999,069 and 3,055,836 are representative of such prior art non-irritating detergent compositions. These compositions generally comprise an amphoteric surfactant combined with an anionic surfactant and a nonionic surfactant in admixture with other ingredients. The amphoteric-anionic surfactant consists essentially of:

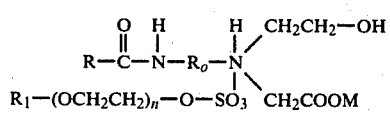

where R is a 9–17 carbon alkyl radical, $R_o$ is an alkylene group of 2–4 carbon atoms, $R_1$ is a member of the group consisting of alkali metals, triethanolamine, mixtures of an alkali metal with hydrogen and mixtures of triethanolamine with hydrogen. The nonionic surfactant portion of the composition is usually a derivative of a 9–18 carbon atom fatty acid monoester of an aliphatic polyhydric alcohol reacted with 10–20 moles of ethylene oxide. The method of forming these compounds is taught in U.S. Pat. No. 2,781,384.

In the reaction products of the formation of the amphoteric surfactant there may also be present some amount of the compound of the formula:

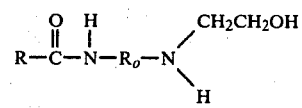

which when reacted with the anionic surfactant forms:

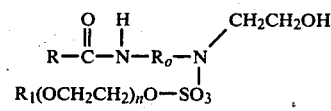

Detergent compositions relatively non-irritating to the eye while providing high foam volume and improved foam stability have also been proposed comprising certain surfactant betaines, an anionic surfactant and a suitable non-ionic surfactant.

These prior art compositions, although they are non-irritating and have good foaming characteristics, have generally low viscosities. Increasing the viscosity of the compositions by employing viscosity building additives or thickeners results in a deterioration of the foaming characteristics of the compositions. Increased viscosity without foam degeneration is desirable in order to formulate detergent compositions, especially non-irritating shampoo compositions.

It has accordingly been the practice hitherto to include in shampoo formulations an ingredient acting as a thickening agent. In the case of the non-irritant compositions already referred to, such thickening agents are typified by polyethylene glycol distearate, for instance polyethylene glycol distearate 6000. The range of substances which can be used for this purpose in non-irritant compositions is somewhat restricted and it is by no means easy to thicken such compositions. Moreover the compatibility of additives to shampoo or other compositions for personal use is hard to predict, especially with regard to irritant properties.

A major drawback involved in the use of thickening agents such as polyethylene glycol distearate, especially if it is desired to adopt a continuous production process for a detergent composition, is that such thickeners are solids. In order to incorporate them into liquid compositions it is necessary to bring them into liquid form, as by melting the thickener and mixing it into the heated composition.

It is an object of the invention to provide a detergent composition formulated from liquid ingredients and fulfilling a desired viscosity requirement.

It is a preferred object of the invention to provide such a composition which is suitable as a non-irritant type of shampoo.

The invention is based on the concept of incorporating in a surfactant ingredient of the composition a chemical structure imparting thickening properties to the substance, for example by introducing groupings characteristic of thickening agents, while maintaining the desired surfactant properties, to provide a liquid ingredient which is thus bifunctional and compatible with the rest of the composition. We have previously proposed to increase the viscosity of detergent compositions of this type to a consistency suitable for marketing as a concentrate in tubes, by employing as non-ionic surfactants the reaction products of certain fatty acid monoesters with a relatively high molar ratio of an alkylene oxide, yielding formulations of viscosity greater than 4000 centipoise at 22°-25° C. In the present invention the concept is extended, to provide alternative and liquid thickening agents in formulations of normal pourable liquid type, by modifying the chemical structure of a non-ionic surfactant in such a way that it presents the aspect of a known thickening agent in having an alkoxylated chain or chains each end of which terminates in certain fatty acid ester groups. This modification is brought about by employing a polybasic acid as a bridge between the chains of alkoxylated non-ionic surfactant compounds of a type previously used in detergent compositions for personal use.

According to the present invention we provide a detergent composition for personal use comprising at least two surfactants, at least one of said surfactants being of the non-ionic type defined below and at least one of said surfactants being of another type. The surfactant of defined type acts as thickening agent and is characterised by the following general formula:

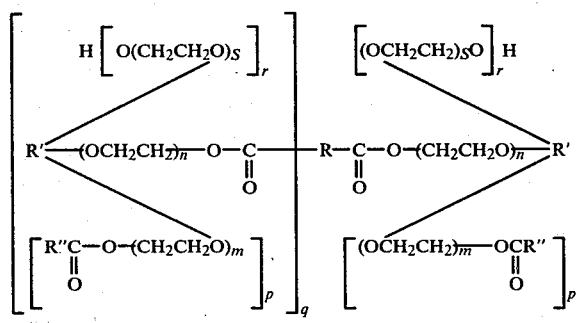

Where
R is a di- or trivalent hydrocarbon group;
R' is di- or higher-valent hydrocarbon group or heterocyclic group;
R" is a monovalent hydrocarbon group containing at least eight carbon atoms;
r and s=0 or an integer;
n, m, p and q are integers, being at least 1; provided that:
n+pm+rs=4 to 100 inclusive
r+p=2 to 7 inclusive
q=1 or 2
and further provided that up to 20 mole percent of the ethylene oxide groups may be replaced by propylene oxide groups.

Preferably R is the hydrocarbon residue of a dibasic or tribasic acid. Examples of such acids are polymethylene diacids such as malonic, succinic, adipic, pimelic, suberic and azelaic acids, polybasic acids or hydroxy acids such as malic, tartaric or citric acids, aromatic acids such as phthalic or trimellitic acids, and unsaturated diacids such as maleic or fumaric acid.

Preferably R' is the hydrocarbon residue or heterocyclic ring-containing residue of a polyol.

Examples of such polyols are sorbitol, sorbitan, isosorbide and mixtures thereof, other pentitol or hexitols or their anhydro-derivatives, pentaerythritol, glycerol or glycols, such as ethylene glycol or propylene glycol.

Preferably R" is a $C_{9-22}$ saturated or unsaturated hydrocarbon group, such as may be derived from mono carboxylic acids having a $C_{9-22}$ hydrocarbon group attached to the acid group. Examples of these are acids derived from natural sources, including lauric, palmitic, oleic, stearic, and myristic acids.

Examples of the non-ionic surfactants thus defined are dibasic acid reaction products of alkoxylated sorbitan fatty esters, for instance, the product having approximately two ethoxylated sorbitan monolaurate groups per succinic acid group.

The non-ionic surfactants to be employed in the invention may be made from their components by processes of etherification and esterification.

Many of the surfactants thus defined possess an unusual property when mixed with water. It is known that certain ethoxylated materials which are miscible with water show an increase in viscosity as the amount of water in the mixture increases. Typically this increase may be of the order of ten times the viscosity of the undiluted surfactant. When a certain critical viscosity is reached, the viscosity falls again at higher water concentrations. With the surfactants defined above the critical viscosity may be a hundred or more times higher than the undiluted surfactant. This viscosity increase effect is advantageous in the preparation of detergent compositions for personal use such as shampoos. The viscosity increasing effect is noted in the presence of ionic and nonionic surfactants.

These nonionic surfactants may be used with another type of surfactant of the most widely varied kinds suitable for personal use. The proportion of the defined nonionic surfactant used in compositions of the invention may vary widely but will generally be in the range from 1 to 20 percent by weight of the composition, more usually from 5 to 15. Preferred compositions according to the invention may be based, as to the surfactant of another type, for instance on the combinations of amphoteric surfactants or betaine surfactants with anionic surfactants already mentioned in connection with non-irritant formulations.

Particularly preferred formulations comprise an amphoteric surfactant combined with an anionic surfactant and a nonionic surfactant of the type herein defined in admixture with other ingredients. The amphoteric/anionic component is described above.

It is envisaged that any anionic surfactant may be used in the detergent composition of the invention such as, for example, an alkyl sulfate of formula $R-CH_2-OSO_3X$, an alkylether sulfate of formula $R(OCH_2CH_2)_p-OSO_3X$, an alkylmonoglyceryl ether sulfonate of formula

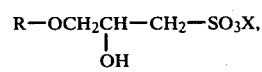

an alkyl monoglyceride sulfate of formula

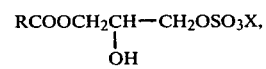

an alkyl monoglyceride sulfonate of formula

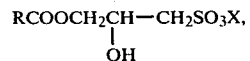

an alkyl sulfonate of formula RSO₃X, an alkylaryl sulfonate of formula

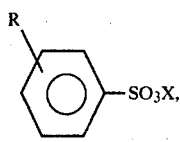

an alkyl sulfosuccinate of formula

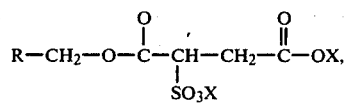

an alkyl sarcosinate of formula

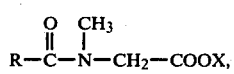

an acyl isethionate of formula

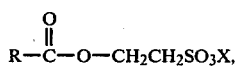

an alkyl methyl tauride of formula

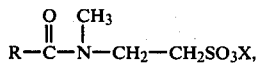

a fatty acid protein condensate of formula

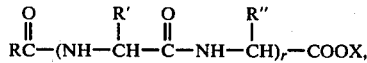

an alcohol ether carboxylate of formula $R(CH_2CH_2O)_q$—COOX, and the like; wherein R is higher alkyl having from 8 to 18 carbon atoms; R' and R" are each hydrogen, lower alkyl, hydroxy-lower alkyl, thio-lower alkyl, carboxy-lower alkyl, amino-lower alkyl, benzyl, or p-hydroxybenzyl; X is an alkali metal ion, alkaline earth metal ion, ammonium ion, or ammonium ion substituted by from one to three lower alkyls; p is an integer from 2 to 6; q is an integer from 2 to 6 and r is an integer from 2 to 10.

The preferred type of anionic surfactant is an alkyl ether sulfate, more preferably sodium tridecylalcohol ether sulfate in which q is about 3.0, known as tridecyl alcohol ether (3.0) sulfate.

The relative amounts of the amphoteric-anionic surfactant that may be used in the preferred final formulation is from about 3 to about 20 percent by weight, for a 34 percent active product and based on the total weight of the composition, the preferred amounts being from 5 to 10 percent. The nonionic surfactant may be present in an amount of from 1 to 20 percent by weight of the total weight of the composition, the preferred amounts being from 5 to 15 percent. The other ingredients in the formulation may include other surfactants, water, stabilizers, additional thickeners, dyes and an acid such as hydrochloric acid to neutralize the formulation. Other ingredients commonly used in the detergent formulations may also be present.

In evaluating the compositions, the irritation test to be employed is the following modified Draize test (see J. H. Draize, et al., Toilet Goods Associations No. 17, May, 1952, No. 1 Proc. Sci. Sect.):

A 0.1 ml of the undiluted sample of the neutral composition under test is dropped into one eye of each of six rabbits. Daily administration of the same quantity of each of the samples is continued for 3 consecutive days. Observations are recorded after one hour, one day, two days, three days, four days and seven days after samples are dropped into the eyes. The extremes of the results will either show substantially no change or only a slight irritation (foreign body effect) in the appearance of the rabbit's eyes after seven days, or severe irritation or complete corneal opacity, as the case may be.

The foam levels are measured by the following method;

The following ingredients are melted together to produce a synthetic sebum:

|  | Percent w/w |
|---|---|
| Lauric Acid | 1.0 |
| Myristic acid | 2.0 |
| Palmitic acid | 7.0 |
| Stearic acid | 5.0 |
| Oleic acid | 15.0 |
| Coconut oil | 15.0 |
| Olive oil | 20.0 |
| Squalene | 5.0 |
| Super Hartolan | 5.0 |
| Light liquid paraffin | 10.0 |
| Spermaceti | 15.0 |
|  | 100.0 |

0.5 grams synthetic sebum and 200 ml tap water are added to 12 g. of the material under test, and the mixture is placed in a 1000 ml stoppered graduated cylinder and inverted once per second for one minute. The final foam volume and its decay over one minute, are noted.

The preferred detergent compositions of the invention may be prepared by first mixing the amphoteric surfactant and the anionic surfactant at ambient temperature until a homogeneous mixture is formed, and then adding the nonionic surfactant and mixing the whole at elevated temperatures (about 50° C.) for about ten minutes until a homogeneous mixture is formed. The pH is then adjusted to 7.2±0.3 by addition of a strong acid (e.g. hydrochloric acid) or a strong base (e.g. aqueous sodium hydroxide solution) as needed.

The preferred detergent compositions of the invention may be used to clean hair and produce high foam volume and good foam stability while also having low ocular irritation and satisfactory viscosity. The detergent compositions of the invention may also be used as liquid soaps or cleansers for cleaning other parts of the human body, animals, inanimate objects and the like.

The preferred detergent compositions of the invention may be combined with water or other suitable solvents to yield the high lathering shampoos of the invention, which have good foam stability and low ocular irritation.

The remainder of the composition when used as a shampoo is normally essentially water, but the shampoo may also contain other thickeners, dyes, perfumes, preservatives, pH adjusters, and the like, as desired.

The invention is illustrated by the following Examples, the nonionic surfactant referred to being the reaction product of succinic acid and ethoxylated sorbitan monolaurate in which there is an average of 20 mols of ethylene oxide per mol of sorbitan and about two ethoxylated sorbitan monolaurate groups per succinic group.

EXAMPLE 1

A detergent formulation was prepared from an aqueous solution of an amphoteric anionic surfactant complex and other detergents. The amphoteric portion of the surfactant was:

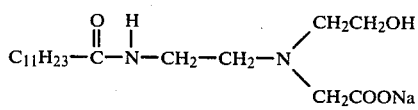

and was reacted with sodium tridecyloxydiethyleneoxyethyl sulphate as set forth in U.S. Pat. No. 2,781,384.

The amounts of the amphoteric-anionic surfactant, shown as a 34 percent active aqueous solution, and the anionic surfactant as 100 percent, are shown in Formula 1 below. The anionic detergent is a 70 percent active aqueous solution of the same material used in the above complex.

The betaine is a 30 percent active aqueous solution of lauric/myristic dimethyl betaine. The pH of the composition was adjusted to $7.0 \pm 0.1$ by the addition of hydrochloric acid. Sufficient deionised water was added so that the total sample weighted 100 grams. The viscosity of the sample, determined at 25° C. by the Brookfield method was 520 cP. The sample was tested for foaming and found to give an initial foam volume of 500 ml of decaying to 220 ml at one minute.

| Formula 1 | |
|---|---|
| | Percent w/w |
| Amphoteric/anionic | 13.7 |
| Anionic | 2.5 |
| Betaine | 2.0 |
| Nonionic surfactant | 12.0 |
| Preservative system | 0.6 |
| Dye and perfume | 0.2 |
| Deionised water | to 100.0 percent |

EXAMPLE 2

A detergent formulation was prepared using the same amphoteric-anionic surfactant and nonionic detergent as in Example 1, the amounts being as shown in Formula 2 below. The pH was adjusted in the same way and water added so that the sample weighed 100 grams. The viscosity of the sample, determined by the Brookfield method, was 680 cP. The sample was tested for foaming and found to give an initial foam volume of 550 ml, decaying to 230 at one minute.

| Formula 2 | |
|---|---|
| | Percent w/w |
| Amphoteric/anionic | 30.1 |

| Formula 2 -continued | |
|---|---|
| | Percent w/w |
| Nonionic surfactant | 11.0 |
| Preservative system | 0.6 |
| Dye and perfume | 0.3 |
| Sorbitan monolaurate | 0.9 |
| Deionised water | to 100.0 percent |

I claim:
1. A low irritating detergent composition for personal use wherein the active ingredients consist essentially of two surfactants as follows:
   (a) from 1 to 20 percent by weight of the total composition of a nonionic surfactant of the following general formula:

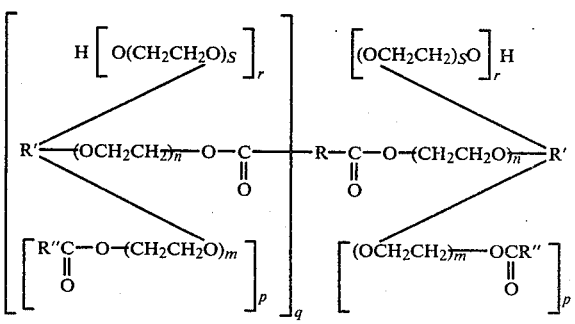

where R is a di- or trivalent hydrocarbon group, R' is a di- or higher-valent hydrocarbon group or heterocyclic group, R" is a monovalent hydrocarbon group containing at least eight carbon atoms, r and s=0 or an integer, n, m, p and q are integers, provided that n+pm+rs=4 to 100 inclusive, r+p=2 to 7 inclusive, q=1 or 2, and further provided that up to 20 mole percent of the ethylene oxide groups may be replaced by propylene oxide groups, and
   (b) from about 3 to 20 percent by weight of the total composition of a surfactant selected from amphoteric/anionic mixtures and betaine/anionic mixtures.

2. A low irritating detergent composition according to claim 1 wherein R is the hydrocarbon residue of a dibasic or tribasic acid, R' is the hydrocarbon residue or heterocyclic ring-containing residue of a polyol and R" is a $C_{9-22}$ saturated or unsaturated hydrocarbon group.

3. A low irritating detergent composition according to claim 2 wherein said nonionic surfactant is a dibasic acid reaction product of an alkoxylated sorbitan fatty ester.

4. A low irritating detergent composition according to claim 3 wherein said dibasic acid is succinic acid and said alkoxylated ester is ethoxylated sorbitan monolaurate having an average of 20 moles of ethylene oxide per mol of sorbitan.

5. A low irritating detergent composition according to claim 3 or 4 containing from 5 to 15 percent of said nonionic surfactant by weight of the composition.

* * * * *